United States Patent
Maeda et al.

[11] Patent Number: 5,810,717
[45] Date of Patent: Sep. 22, 1998

[54] BENDING MECHANISM AND STEREOSCOPE USING SAME

[75] Inventors: Shigeo Maeda; Katsunori Hosotani; Osamu Tohyama, all of Itami, Japan

[73] Assignee: Mitsubishi Cable Industries, Ltd., Amagasaki, Japan

[21] Appl. No.: 710,647

[22] Filed: Sep. 18, 1996

[30] Foreign Application Priority Data

Sep. 22, 1995 [JP] Japan ................................ 7-269272
Mar. 21, 1996 [JP] Japan ................................ 8-093102
Apr. 24, 1996 [JP] Japan ................................ 8-129197

[51] Int. Cl.⁶ ............................................. A61B 1/00
[52] U.S. Cl. ........................ 600/151; 600/146; 600/143
[58] Field of Search .................................. 600/146, 147, 600/148, 149, 150, 151, 152, 143, 166

[56] References Cited

U.S. PATENT DOCUMENTS

| | | | |
|---|---|---|---|
| 4,790,624 | 12/1988 | Van Hoye et al. | 600/151 X |
| 4,977,886 | 12/1990 | Takehama et al. | 600/151 |
| 4,987,314 | 1/1991 | Gotanda et al. | 600/151 X |
| 5,482,029 | 1/1996 | Sekiguchi et al. | 600/143 X |
| 5,624,380 | 4/1997 | Takayama et al. | 600/151 X |

FOREIGN PATENT DOCUMENTS 533050  3/1993  European Pat. Off. ................ 600/151
4-8338  1/1992  Japan ................................ 600/151

*Primary Examiner*—Beverly M. Flanagan
*Attorney, Agent, or Firm*—Wenderoth, Lind & Ponack, L.L.P.

[57] ABSTRACT

A bending mechanism for use with a stereoscope, comprises a tubular body or linear body having a bending part, a movable part which can move in the lengthwise direction of the tubular body or linear body, two actuators formed to act in opposition to each other via the movable part, and a pull wire which extends in the lengthwise direction along the bending part. One end of the wire is fixed to one end side of the bending part and the other end of the wire is fixed to the movable part set at the other end side of the bending part. At least one of the two actuators is a shape memory element. The bending mechanism of the present invention is free from displacement of the movable part when bending action is not needed, since the two actuators are used which act in opposition to each other via the movable part, and thus, buckling of the bending part can be prevented. The simple structure of the activator unit of the present invention facilitates a reduction of the size of the structure. The stereoscope of the present invention is free from buckling of the image guide and the like, and the angle of convergence can be adjusted easily and a desired three-dimensional view can be obtained easily.

18 Claims, 11 Drawing Sheets

BENDING MECHANISM AND STEREOSCOPE USING SAME

FIELD OF THE INVENTION

The present invention relates to a mechanism capable of bending a bending part by activating an actuator of a shape memory element, and further to a stereoscope utilizing said mechanism.

BACKGROUND OF THE INVENTION

A tip articulation mechanism has been conventionally used for bending a tip articulation endoscope used for observation of sites difficult to see by a normal technique, such as the inside of small tubes and the human body. As such tip articulation endoscope, there has been developed one wherein the distal end portion of the endoscope and the operation end at the proximal side are connected by a pull wire, and wherein an operator manipulates an operation nob attached to the above-mentioned operation end to pull the wire to cause articulation of the tip of the endoscope. This type of tip articulation endoscope requires highly skilled manipulation and is barely an ideal mechanism.

Thus, a tip articulation endoscope has been proposed which aims at mechanical operation by the use of a shape memory alloy for the tip articulation mechanism. For example, there have been proposed one wherein the above-mentioned pull wire is made from such a shape memory alloy, and upon heating, the wire shrinks to bend the inserted tip of the endoscope, so as to operate by pulling the tip by the wire as mentioned above; and one equipped with a shape memory alloy coil at the end portion of the above-mentioned pull wire, wherein, upon heating of the shape memory alloy coil, the shape memory alloy coil moves to pull the wire to bend the inserted tip of the endoscope.

A specific example of the latter endoscope is shown in FIG. 12, which is a two direction articulation endoscope comprising an endoscope 5 attached to a tip articulation mechanism. The tip articulation mechanism comprises shape memory alloy coils 2a and 2b, which memorize close coiling state of the coils and are set, after stretching, in an outer tube 7 in parallel with the lengthwise direction of the tube, as well as pull wires 4a and 4b fixed, at first ends thereof, to the end-most part of a tip articulation part 1b and, at second ends thereof, to the above-mentioned shape memory alloy coils 2a and 2b.

The principle of this mechanism is as follows. That is, the tip articulation endoscope is bent toward the pull wire 4a side upon heating of the shape memory alloy coil 2a, which causes shrinking of the coil 2a to pull the wire 4a, as shown in FIG. 12. When heating is stopped, the shape memory alloy coil 2a undergoes reverse transformation to weaken the pull force so that the pull forces of the shape memory alloy coils 2a and 2b are balanced, whereby the articulation part is no longer bent but is rather linear. At this point, elasticity (i.e., pull force) is the same for both shape memory alloy coils 2a and 2b when cooled, and the movement is balanced. However, the tip articulation part 1b is under application of force by the above-mentioned two shape memory alloy coils 2a and 2b .

In addition, there has been proposed a stereoscope having two image guides, each guide having the above-mentioned tip articulation mechanism to individually change the angle of convergence of image guides. In this mechanism, since the angle of convergence is individually changed by each image guide, a desired stereoscopic image is difficult to obtain and a complicated three-dimensional target cannot be observed accurately.

The above-mentioned tip articulation mechanism using the former type of shape memory alloy wire is not practical, since it requires a considerable length of the shape memory alloy wire to enable sufficient tip articulation. Those using the latter type of shape memory alloy coil are subject to buckling of the tip articulation part of the endoscope due to the pull force applied by elasticity which pulls the wire not only during heating but also cooling, thus necessitating the provision of another member to prevent such buckling. Such additional member leads to a greater force needed for the bending action, which in turn creates the need to enlarge the shape memory alloy coils, so that the endoscope cannot be made smaller in diameter. When the same, conventional shape memory alloy coil is used, the degree of tip articulation becomes smaller to cause a different problem.

When the above-mentioned tip articulation mechanism is applied to a stereoscope, two image guides are respectively associated with the problem of buckling. In addition, the two image guides which function individually make their control difficult and a desired stereovision cannot be obtained with ease.

It is therefore an object of the present invention to provide a bending mechanism which allows an endoscope to be made smaller in diameter and which is free of buckling in the bending part. It is also an object of the present invention to provide a stereoscope capable of forming a desired stereoscopic image with ease by co-activating two image guides.

SUMMARY OF THE INVENTION

The bending mechanism of the present invention comprises a tubular body or linear body having a bending part, a movable part which can move in the lengthwise direction of the tubular body or linear body, two actuators formed such that they antagonize (i.e. act in opposition to) each other via the movable part, and a pull wire which extends in the lengthwise direction along the bending part. One end of the wire is fixed to one end portion of the bending part and the other end of the wire is fixed to the movable part set at the other end portion of the bending part. At least one of the two actuators is a shape memory element.

The two actuators are subject to no particular limitation as long as at least one of them is a shape memory element and they antagonize (i.e. act in opposition to) each other via the movable part. Both of the actuators are preferably shape memory elements, since quick responses in, for example, recovering the movable part to the original position (elimination of bending) can be attained as a result of independent activation of the actuators. It is also beneficial to use the same shape memory element for both actuators, because it facilitates designing of the bending mechanism and control of the bending. The above-mentioned antagonization means that the two actuators are activated in directions that balance the force of each actuator.

The bending mechanism of the present invention is more beneficial when the two actuators are shape memory elements, and two pull wires are used where one actuator pulls one wire and the other actuator pulls the other wire, thus enabling bending in two directions.

When bending in two directions is desired, the pull wire only needs to be pulled toward the proximal end of the bending mechanism by the action of the above-mentioned actuator. As shown in FIG. 2, for example, either end of a first pull wire (e.g., 4a) is extended along the bending part and the other end thereof is fixed to the movable part, and either end of a second pull wire (e.g., 4b) is extended along the bending part and the other end thereof is fixed to the movable part via a pulley formed on the proximal end portion of the tubular body outside the movable range of the movable part; or at least either one of the above-mentioned pull wires is wound around a pinion working with a rack (movable part in this example).

When bending in a number of directions is desired, two or more pull wires of shape memory alloy coils are used which can be heated individually. When the shape memory alloy coil is heated, the coil comes to have a greater spring constant than an unheated coil. As a result, when an actuator is activated to draw a pull wire, the coil shows smaller elongation, and the pull wire of shape memory alloy coil having a smaller elongation becomes shorter than other pull wires to cause bending in the direction of the shorter wire side. Thus, the shape memory alloy coil to be heated should be appropriately determined to attain bending in a desired direction. This design is simple in construction as compared to an embodiment where plural activator units are contained as described later, and is suitable for miniaturization.

The present invention is advantageous in that the bending part can be bent in numerous directions by forming plural actuator units wherein one actuator unit comprises two actuators, a movable part and a pull wire, one end of each pull wire of the plural actuator units being extended at a predetermined circumferential position of the bending part, and the other end of each pull wire being fixed to each movable part of the actuator units, whereby the bending part can be beneficially bent in many directions.

For forming plural actuator units to allow bending in a number of directions, for example, two actuator units are disposed in the radial direction of the tubular body as shown in FIG. 5, and the pull wires of the aforementioned two actuator units are set at the predetermined circumferential positions and extend in the direction of the above-mentioned bending part, which positions correspond to desired bending directions (180° opposite positions in FIG. 5). Alternatively, as shown in FIG. 6, the movable part is divided in the circumferential direction of the tubular body (divided into four in FIG. 6), and two actuators and pull wires are set on each of the divided movable parts to give plural actuator units, wherein one end of the pull wires in the actuator unit is set at the predetermined circumferential position and extend in the direction of the above-mentioned bending part, which position corresponds to desired bending directions (in four directions spaced apart by 90° in FIG. 6).

The shape memory element of the actuator is not particularly limited in terms of material and shape, and shape memory alloys and shape memory polymers can be used, and the material thereof may be coil materials, linear materials, plate materials, and the like. Preferred is a shape memory alloy coil, since the actuator can easily be made smaller and thin by using such a coil which can increase displacement of the movable part without significant decrease in driving force (shape recovery force) as compared to linear materials and plate materials.

It is also preferable to form plural shape memory elements in an actuator, because the size of one shape memory element can be reduced. For example, when the movable part is a ring, smaller shape memory elements can be disposed at about equal intervals in the circumferential direction of a tubular body, and when the movable part is square, they may be disposed at corners. When they are formed in this manner, the force of the shape memory elements can be uniformly transmitted to the movable part.

The plural shape memory elements are preferably heated by application of a current, since serial electric connection thereof for this end makes it possible to decrease the size of the tubular body or linear body and the current for activation.

The movable part is subject to no particular limitation as long as it can move in the lengthwise direction of the scope and can be determined as appropriate in terms of shape. The preferred shape thereof is a ring shape. By mounting the actuators 2a and 2b, and movable part 3 on a tubular body 1, the diameter of the tubular body can be reduced and a greater inside space can be secured. For example, one or more working channels can be formed, in which a laser guide optical fiber, a pressure sensor, a tactile sensor, a PH sensor and the like are inserted to additionally impart laser irradiation function and various sensor functions, whereby a multi-functional endoscope can be provided.

When a control means is formed on a power supplying means of the actuator of the bending mechanism, the bending angle can be optionally determined. Specifically, for example, when the actuator is a shape memory alloy and the mechanism is activated upon heating by a current, the current is pulsed, so that the amount of current can be varied by pulsing to control heating of the shape memory alloy. As a result, shape recovery deflection (driving amount), namely, pull amount of the pull wire can be controlled to adjust the bending angle.

The stereoscope of the present invention comprises two image guides, each having a bending part, which are disposed at a certain distance, a movable part capable of freely moving in the lengthwise direction of the image guide, two actuators formed to antagonize (i.e. act in opposition to) each other via the movable part, and a pull wire with one end thereof formed along the bending part and the other end fixed to the movable part, wherein at least one of the two actuators is a shape memory alloy element, and operation of the pull wire activates the bending parts of the two image guides to make them approach each other.

Inasmuch as the two image guides can be co-activated by a coupling wire connecting the two image guides at the distal end portion thereof, with one end of the pull wire connected to the coupling wire and the other end to a movable part, the angle of convergence can be adjusted and controlled to obtain a desired image of three-dimensional targets. By the angle of convergence is meant the angle formed by the axial direction of the image guide before pulling and the axial direction after pulling.

When two pull wires are used with the end portion of each one of them connected to the end portion of the two image guides and the other end connected to the movable part, a space can be formed between the two image guides, and various functions can be established using the space.

In addition, a stopper to limit displacement of the movable part obviates contact of the two image guides when the angle of convergence is changed, which in turn decreases a potential for failure of a scope. The stopper may comprise, for example, a displacement limiting control rod which is attached to the movable part in such a manner that it penetrates through a control window formed therein, so that the displacement occurs only in the region of the opening of the control window.

DETAILED DESCRIPTION OF THE INVENTION

The present invention is described in more detail in the following.

Figure 1:
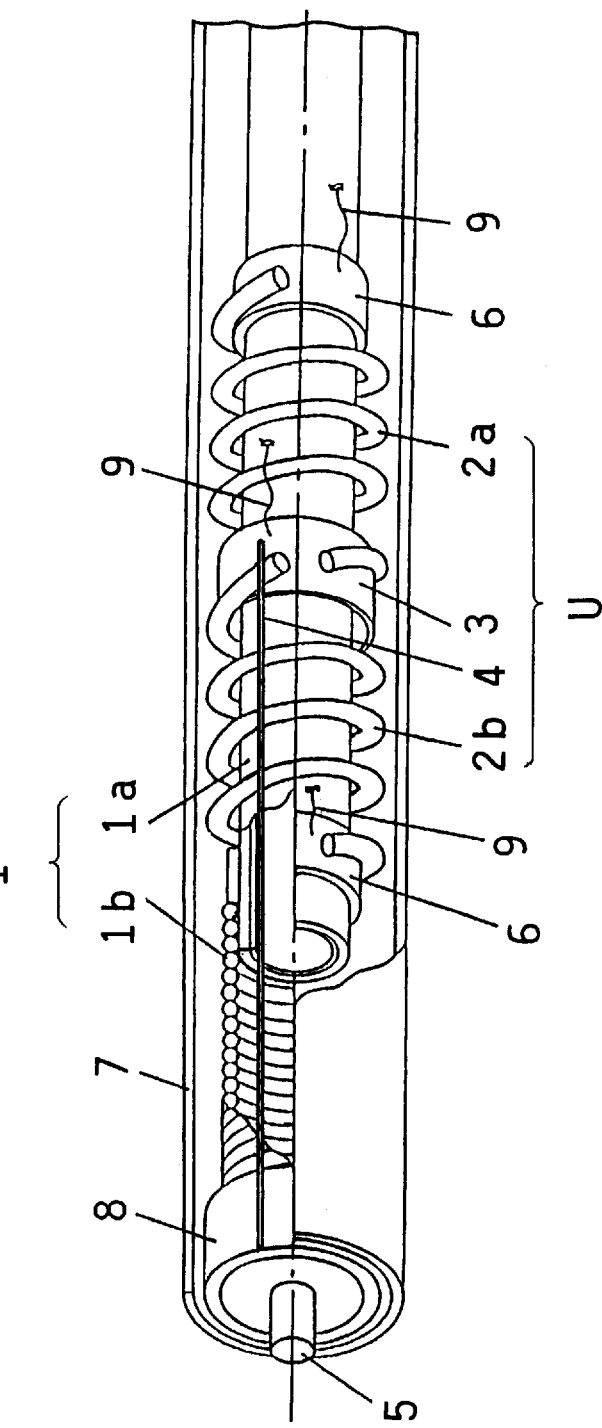
FIG. 1 is a cross-sectional view, partially broken away, of one embodiment of a bending endoscope using a bending mechanism of the present invention.

FIG. 1 shows one embodiment of a bending mechanism of the present invention. In this Figure, 1 is a tubular body consisting of a main body 1a and a bending part 1b mounted on the distal end of the body. At an end portion of the main body 1a, a movable part 3 is movably mounted for movement in the lengthwise direction of the tubular body 1, and an actuator 2a of a shape memory alloy coil and an actuator 2b of the same shape memory alloy coil are installed to antagonize (i.e. act in opposition to) each other via the movable part 3. A pull wire 4 extends in the lengthwise direction along the bending part 1b. One end of the wire 4 is fixed to one end portion of the bending part 1b and the other end of the wire 4 is fixed to the movable part 3.

According to this construction, the activation forces of actuators 2a and 2b are balanced against each other and not transmitted to the movable part 3 in a normal state when the actuators are not in operation. Thus, no pull force is applied to the pull wire 4 fixed to the movable part 3. As a result, bending part 1b is not subject to a force and is free of buckling. When this part is to be bent, the actuator 2a is activated by making the shape memory alloy coil in the present embodiment recover to the original shape thereof to alter the balance between the actuators 2a and 2b, to thereby move the movable part 3. Thus, a pull force is applied to the pull wire 4 to cause bending of the bending part 1b.

In the bending mechanism of the present invention, the tubular or linear body 1 only needs to comprise a flexible bending part 1b, and may be exemplified by a tubular or linear body having flexibility in the entirety thereof, an inflexible tubular or linear body connected with a flexible member as a bending part, or the like.

The actuators 2a and 2b only need to be able to act in opposition to each other via the movable part, and may be disposed serially or in a parallel relationship in the lengthwise direction of the tubular body via the movable part. The former serially disposed actuators are easily fabricated and suitable for small size scopes. The latter parallel actuators are suitable when heating by light is intended, since both actuators can be heated easily. When heating by light is applied, the actuators may be tapered in the lengthwise direction, so that the actuators can be heated over their entire lengths, which is preferable for materials with poor thermal conduction, such as TiNi shape memory alloy and the like.

The movable part 3 is not particularly limited, and is optionally designed according to the mode of use. When a shape memory alloy coil is used for the actuator and the actuator is heated by a current, for example, a conductive material is preferably used for easy connection with a lead wire. When a shape memory alloy coil is heated by a current, however, an insulating material should be used to connect the shape memory alloy coil dynamically in parallel and electrically in series, when plural shape memory alloy coils are used in a single actuator.

The movable part 3 and two actuators 2a and 2b may be prepared from a single shape memory alloy coil. That is, one shape memory alloy coil is placed in the lengthwise direction of a tubular body, a pull wire 4 and a lead wire for grounding are fixed to the center portion in the lengthwise direction of the shape memory alloy coil, and lead wires are connected to both ends of the shape memory alloy coil to enable separate heating of the distal end side and the proximal end side divided by the center portion in the lengthwise direction of the shape memory alloy coil. Consequently, the center portion in the lengthwise direction of the shape memory alloy coil functions as a movable part, and the distal end portion and the proximal end portion of the shape memory alloy coil function as two actuators. This construction simplifies the structure by obviating the connection between the movable part and actuators, which is suitable for miniaturization and easy fabrication.

While the pull wire 4 is not particularly limited, a material with low elongation is preferably used. This is because pull wire 4 is preferably devoid of stretching by pulling, so that a stable operation can be secured during bending and repetitive bending.

When an image guide is placed in the inside of the tubular body, a bending endoscope can be easily fabricated. The image guide is not subject to any particular limitation as long as it is flexible, and silica fibers and multi-component fibers can be used. The image guide may be used alone or in combination with a light guide to form an image scope.

While the above-mentioned embodiments concern a tubular body having a bending part at a distal end, the bending mechanism of the present invention is not limited to this structure. For example, plural bending mechanisms may be serially formed on a tubular body to allow bending of the tubular body in multiple degrees of freedom. Moreover, the tubular body may be a linear body.

Figure 8:
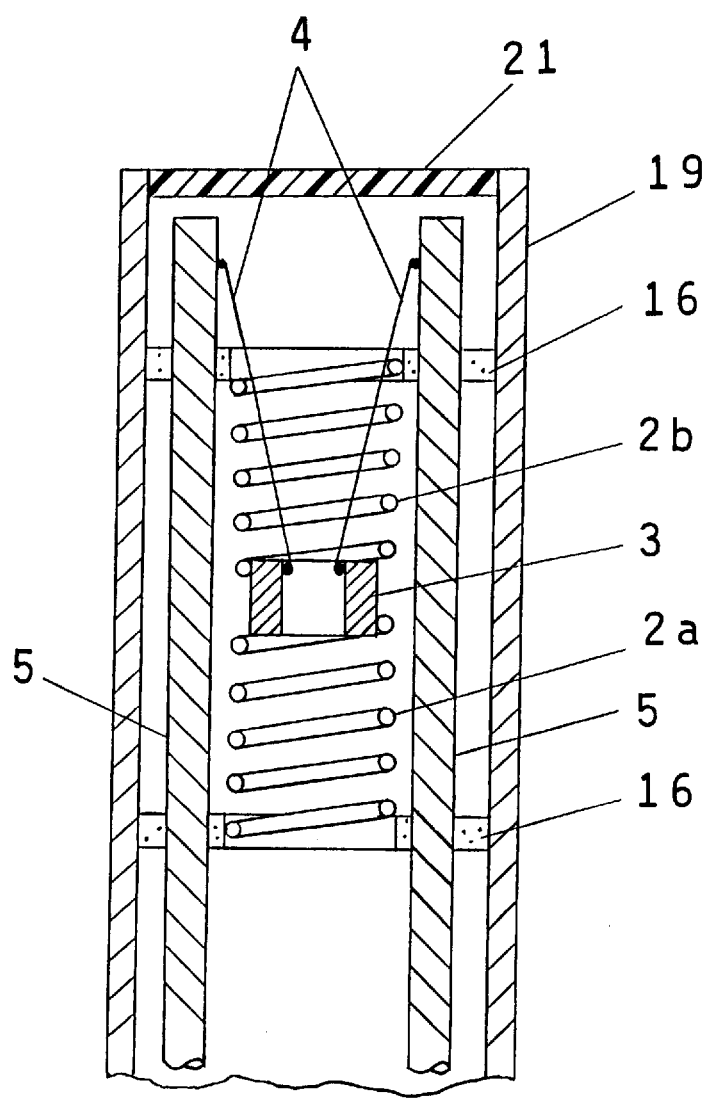
FIG. 8 is a lengthwise cross-sectional view of a stereoscope of the present invention.

FIG. 8 shows one embodiment of the stereoscope of the present invention. As illustrated, a movable part 3 is movably provided in the scope for movement in the lengthwise direction, and two actuators 2a and 2b of shape memory elements are disposed on both sides of the movable part 3 to allow their antagonistic (i.e. opposing) action. Image scopes 5, 5 are installed in a parallel relationship with the movable part 3 and actuators 2a and 2b, interposed therebetween, and the image scopes 5, 5 are supported by support plates 16, 16 which also fix the actuators 2a and 2b. The image scopes 5, 5 can be bent, as bending parts, at the distal portion outside of the distal support plate 16. The actuators 2a and 2b are fixed, at first ends thereof, to the support plates 16, 16. The pull wires 4, 4 are fixed, at first ends thereof, to movable part 3 and, at second ends thereof, to end portions of the image scopes 5, 5.

According to this construction, the movable part 3 moves downward in FIG. 8 when the shape memory element 2a is heated to recover to its original shape, thereby pulling the wires 4, 4. In consequence, the bending parts of the image scopes 5, 5 are bent as in the above-mentioned bending mechanism to change the angle of convergence and to obtain a three-dimensional image.

The present invention is not limited to the above-mentioned embodiments with regard to the movable part, actuators, pull wires, image guide and the like of the stereoscope, and those similar to the foregoing various modes described with respect to bending mechanism can also be used.

EXAMPLE 1

The present invention is described in detail by way of specific examples in the following.

In this Example, a bending endoscope as shown in FIG. 1 was fabricated. A tubular body 1 comprising a main body 1a (outer diameter 1.0 mm) of a stainless pipe (inner diameter 0.7 mm, outer diameter 0.8 mm) coated with polyimide for insulation, and a stainless close coiled bending part 1b (outer diameter 1.3 mm, strand diameter 0.15 mm) was used. On the periphery thereof, a first actuator 2a of a TiNi shape memory alloy coil spring which was close coiled with a strand diameter of 0.25 mm, outer diameter of 1.6 mm and length of 6 mm and made to store this coiling state, and a second actuator 2b of the same shape memory alloy coil spring were serially provided in the lengthwise direction of the tubular body 1 in such a manner that the length of the coil spring became 20 mm. A movable stainless ring 3 (inner diameter of 1.3 mm, and outer diameter of 1.4 mm) was set between the two coil springs 2a and 2b to which the end portions of the two springs were attached. Stainless actuator fixing members 6, 6 (inner diameter of 1.0 mm, and outer diameter of 1.2 mm) were provided at the other end portions of the coil springs. The actuator fixing members 6, 6 were fixed to the main body 1a. A 0.08 mm diameter stainless pull wire 4 was fixed to the distal end of the bending part 1b at one end thereof, and the other end thereof was fixed to the movable ring 3 through the bending part 1b. An image scope 5 (outer diameter of 0.4 mm) was set in the tubular body 1, and a polyurethane outer tube 7 (inner diameter of 1.8 mm, and outer diameter of 2.0 mm) was applied. In this Example, the outer tube 7 in combination with bending part 1b functioned as a guide wire for pull wire 4.

The above bending endoscope was fabricated as in the following. The shape memory-treated coil springs 2a and 2b were fixed to movable stainless ring 3 at first ends of the springs and to actuator fixing members 6, 6 at second ends thereof. These were assembled onto the main body 1a with the first actuator coil spring 2a at the proximal side, and the actuator fixing member 6 at the second actuator coil spring 2b side was fixed to one side of the main body 1a, leaving an end portion of the main body 1a part to be fixed to the bending part 1b. The coil springs 2a and 2b were each stretched to 20 mm, and the other actuator fixing member 6 was fixed to the main body 1a. In this Example, the two coil springs were the same and either coil could be inserted into the main body 1a first. Then, the end portion of the stainless bending coil 1b was fixed to the above-mentioned end portion of the stainless pipe of the main body 1a, and a stainless end ring 8 (inner diameter of 1.3 mm, and outer diameter of 1.6 mm) was fixed to the other end of the stainless coil 1b. In doing so, the portion of the stainless coil 1b which was not fixed was 30 mm in length of the bending part. One end of pull wire 4 was fixed to the above-mentioned movable ring 3, and the other end was fixed to end ring 8. Lead wires 9, 9, 9 were connected, at first ends thereof, to movable ring 3, and actuator fixing members 6, 6, respectively. Outer tube 7 was applied, and image scope 5 was inserted into the tubular body 1, which was followed by fixing to thereby constitute an endoscope.

The prepared endoscope functioned according to the following principle. The first actuator shape memory coil spring 2a was heated by a current from a power source (not shown). The coil spring 2a recovered its original close coiled state to cause displacement of movable ring 3 to the proximal side, whereby pull wire 4 was pulled to cause bending of the bending part.

In this Example, a shape memory coil spring 2b was used for the second actuator, and heating of coil spring 2b enabled quick recovery of the initial state (without bending) after bending of the tip.

EXAMPLE 2

Figure 2:
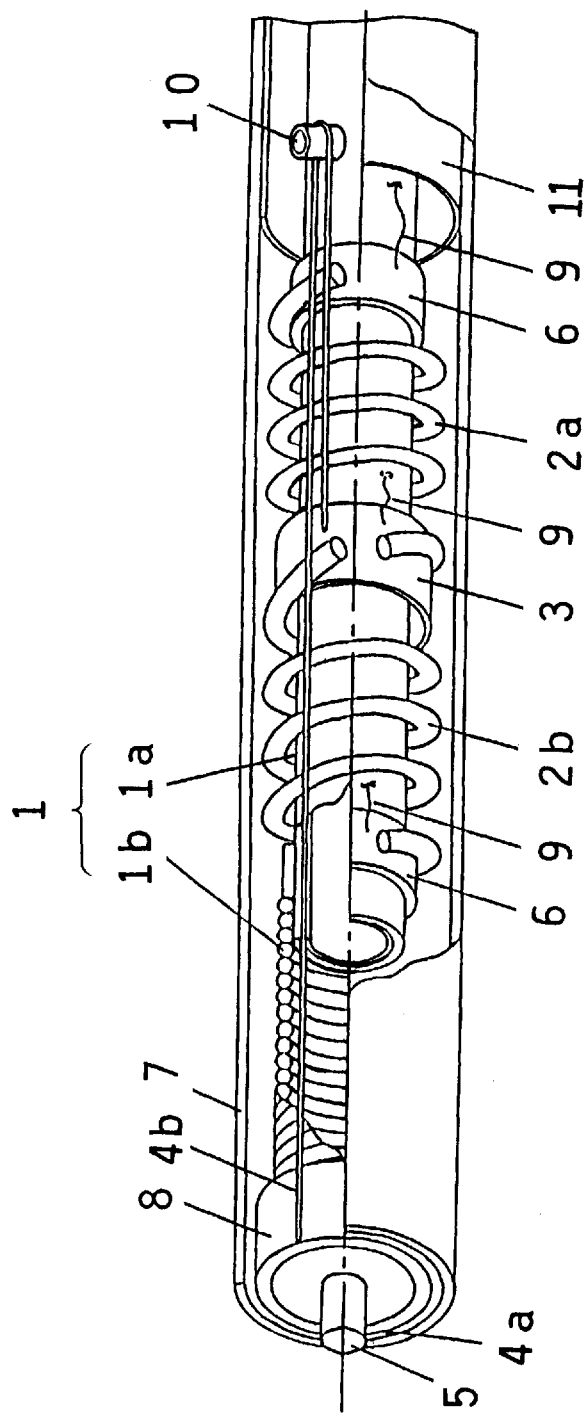
FIG. 2 is a cross-sectional view, partially broken away, of another embodiment of a bending endoscope using the bending mechanism of the present invention.

A two direction bending endoscope as shown in FIG. 2 was fabricated. The parts in common with Example 1 were prepared in the same manner as in Example 1 using the same materials.

The members used only in this Example were a second pull wire 4b different from the pull wire used in Example 1 only in length, pulley 10 formed of a stainless pipe (inner diameter of 1.3 mm, and outer diameter of 1.4 mm) and a pulley support tube 11 formed of a stainless pipe (inner diameter of 1.7 mm, and outer diameter of 1.8 mm) to support the above pulley 10 and the main body 1a.

The two direction bending endoscope was fabricated as follows. A hole was formed in each of the pulley support tube 11 and the main body 1a at the proximal side from the actuator fixing member 6 attaching to one end of the first actuator shape memory coil spring 2a, and the pulley 10 was fitted into both holes. In the same manner as in Example 1, coil springs 2a and 2b, movable ring 3 and actuator fixing member 6 were assembled and fixed to the main body 1a, and bending part 1b and end ring 8 were fixed in place. Then, the first pull wire 4a was set in the same manner as in Example 1, and one end of the second pull wire 4b was fixed to the end portion of the bending part 1b at the opposite position from the first pull wire 4a, and the other end thereof was fixed to movable ring 3 via pulley 10 through the bending part 1b. Lead wires 9, 9, 9 were connected to movable ring 3 and actuator fixing members 6, 6, respectively, at one end. Outer tube 7 was applied, and image scope 5 was inserted into the tubular body 1, which was followed by fixing to constitute an endoscope.

While the principle of action of the two direction bending endoscope was the same as in Example 1, when the second actuator shape memory coil spring 2b was heated by a current, the second pull wire 4b was pulled toward the distal end at the portion fixed to the movable ring 3 and, being reversed by the pulley 10, drawn to the proximal end at the bending part 1b. Therefore, the bending part 1b was bent in a direction opposite from the bending direction in which it was bent when the first actuator shape memory coil spring 2a was heated.

EXAMPLE 3

Figure 3:
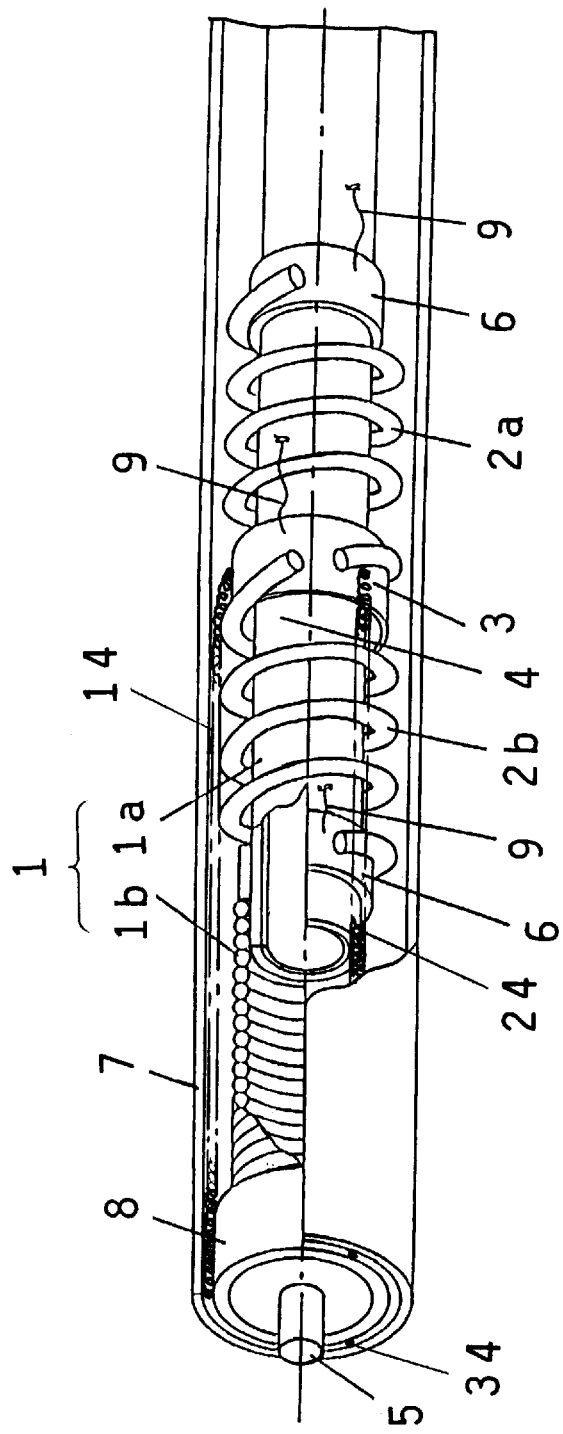
FIG. 3 is a cross-sectional view, partially broken away, of still another embodiment of a bending endoscope using the bending mechanism of the present invention.

This Example relates to a multi-direction bending endoscope using a shape memory alloy coil for a pull wire as shown in FIG. 3. In addition to the structure of Example 1, three shape memory alloy coils (strand diameter of 0.03 mm, and outer diameter of 0.09 mm) were used as pull wires 14, 24 and 34 which were placed in the circumferential direction at equal intervals. First ends of the respective pull wires 14, 24 and 34 were fixed to the distal end of the bending part 1*b*, and second ends of the pull wires were fixed to the movable ring 3. The shape memory alloy coils were each connected to lead wires (not shown) and could be heated separately. The actuator shape memory alloy coils 2*a* and 2*b* were close-coiled with a strand diameter of 0.3 mm, an outer diameter of 1.6 mm, a length of 9 mm and were so as to store (or retain) this coiling state. The coils were stretched to 24 mm and attached at their respective ends to the distal end of the bending part 1*b* and the removable ring 3. Other than the pull wires and actuators, the structure of the endoscope of Example 3 is the same as in Example 1.

The prepared multi-direction endoscope functioned according to the following principle. As in Example 1, the actuator shape memory coil spring 2*a* was heated by a current from a power source (not shown). The coil spring 2*a* recovered its original close coiling state to cause displacement of movable ring 3 to the proximal side, whereby pull wires 14, 24 and 34 were pulled. Of these shape memory pull wires 14, 24 and 34, for example, only pull wire 14 was heated. Thus, the heated wire 14 had a greater spring constant than other wires 24 and 34, so that when pulled, it showed small elongation or scarce elongation. Therefore, the wire 14 alone was pulled in the absence of elongation, when wires 24 and 34 were only stretched, thereby causing bending of bending part 1*b* toward pull wire 14. Selective heating of the three pull wires 14, 24 and 34 enabled bending in three directions. In addition, control of the heating of the three pull wires 14, 24 and 34 enabled bending in numerous directions. For example, when only wires 14 and 24 were heated, the scope bent in a direction toward a location in between wires 14 and 24.

EXAMPLE 4

Figure 4:
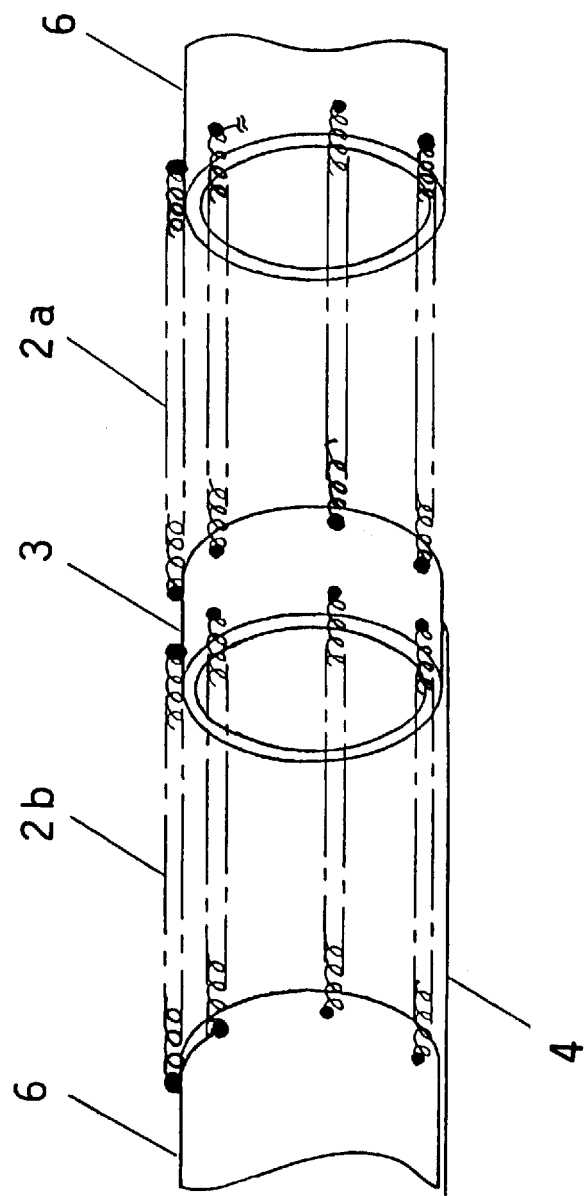
FIG. 4 is a perspective view showing an actuator unit of the bending mechanism of the present invention.

A modified actuator unit U comprising two actuators, a movable part and a pull wire fixed at one end to the movable part was used in this Example, which is shown in FIG. 4. In FIG. 4, all actuator shape memory coil springs are not shown, for simplification. In fact, the first and second actuators 2*a* and 2*b* each consisted of 13 TiNi shape memory alloy coil springs close-coiled with a strand diameter of 0.1 mm, an outer diameter of 0.3 mm, and a length of 18 mm and so as to store this coiling state. The shape memory alloy coil springs were set in the circumferential direction of the tubular body at about equal intervals, and were fixed at first ends to the movable stainless ring 3 (inner diameter of 1.3 mm, and outer diameter 1.4 mm) and to actuator fixing members 6, 6 (inner diameter of 1.0 mm, outer diameter of 1.2 mm) at the other end. The 13 coils of 2*a* or 2*b* were electrically connected serially. Then, one end of pull wire 4 was fixed to the movable ring 3 to constitute an actuator unit U. When this actuator unit U was provided on the bending endoscope of Example 1, the length of shape memory alloy coil springs was adjusted to 25 mm, thereby attaining bending of about 60 degrees.

EXAMPLE 5

Figure 5:
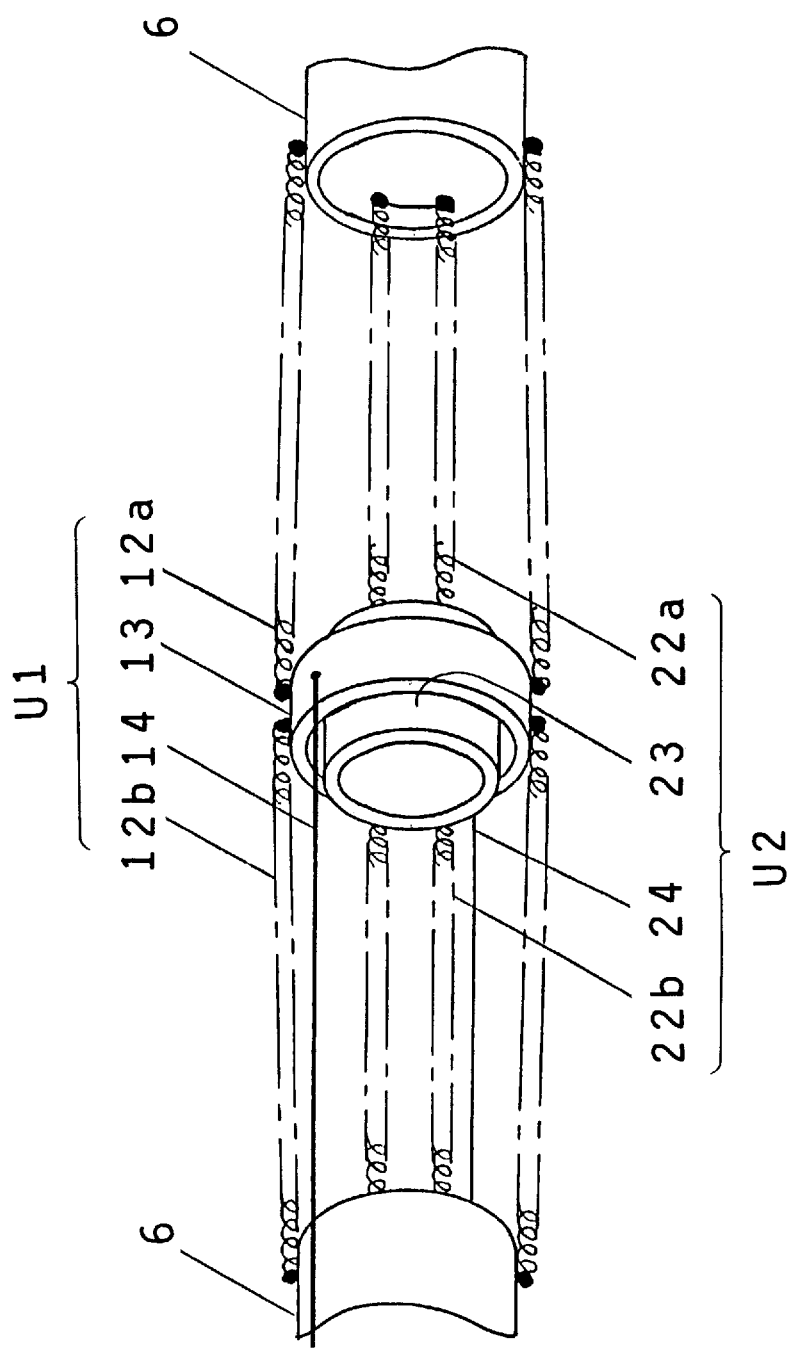
FIG. 5 is a perspective view showing another actuator unit of the bending mechanism of the present invention.

The modified actuator units U were set in duplicate as shown in FIG. 5. The two actuator units U were fabricated in the same manner as in Example 3 except for the size of each member. Actuators 12*a*, 12*b*, 22*a* and 22*b* each consisted of 6 TiNi shape memory alloy coil springs close-coiled at a strand diameter of 0.1 mm, an outer diameter of 0.3 mm, a length of 20 mm and were made so as to store this coiling state. The outer movable ring 13 was a stainless ring having an inner diameter of 1.3 mm and an outer diameter of 1.4 mm, and the inner movable ring 23 was a stainless ring having an inner diameter of 1.1 mm and an outer diameter of 1.2 mm. The actuator fixing members 6, 6 were stainless rings having an inner diameter of 1.0 mm and an outer diameter of 1.2 mm. When they were applied to the bending endoscope of Example 1, the length of shape memory alloy coil springs was adjusted to 28 m, thereby attaining bending of about 60 degrees in two directions.

EXAMPLE 6

Figure 6:
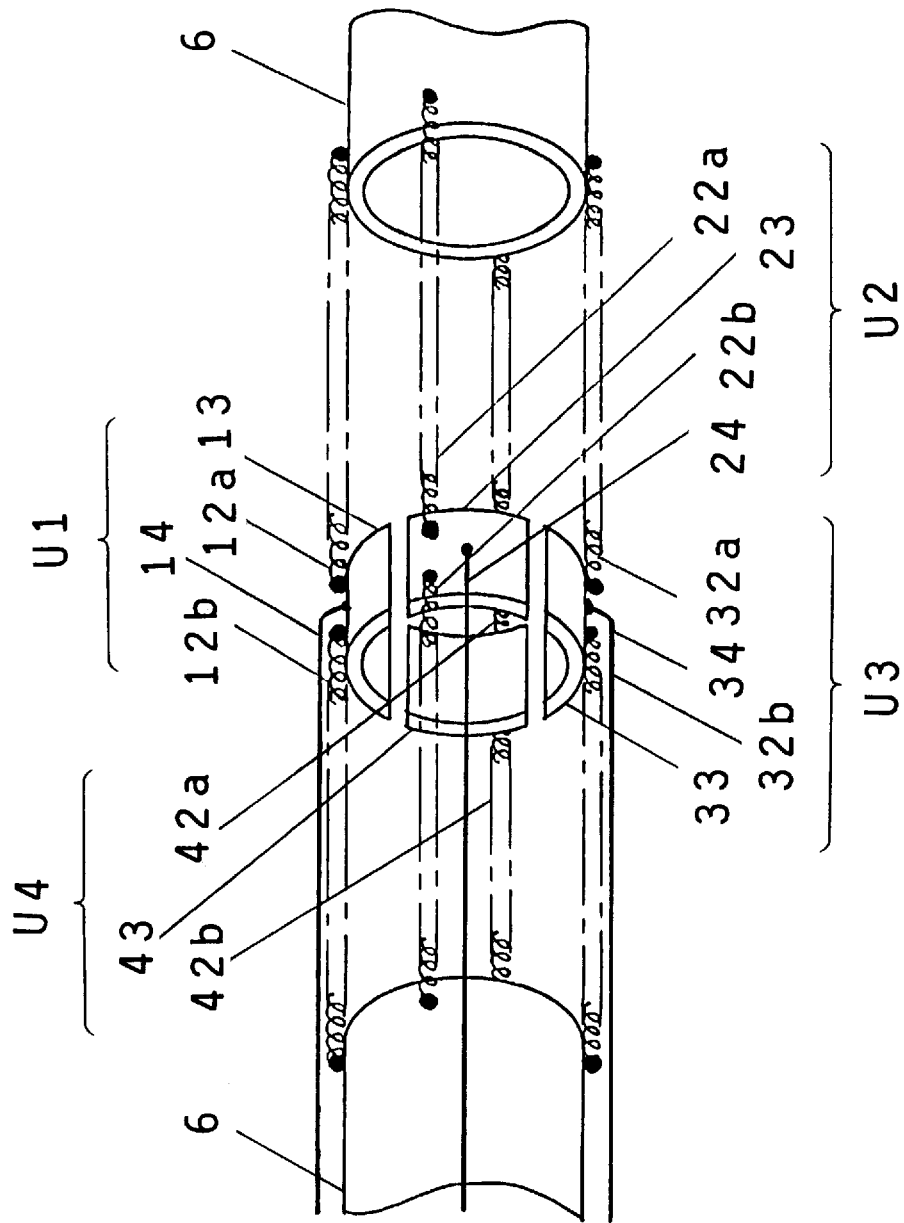
FIG. 6 is a perspective view showing still another actuator unit of the bending mechanism of the present invention.

This Example relates to an endoscope wherein the movable part was divided in the circumferential direction as shown in FIG. 6.

A stainless ring (inner diameter of 1.3 mm, and outer diameter of 1.4 mm) was divided into four parts in the circumferential direction of the tubular body to result in movable parts 13, 23, 33 and 43. Actuators 12*a*, 12*b*, 22*a*, 22*b* . . . , each consisting of 3 TiNi shape memory alloy coil springs close-coiled at a strand diameter of 0.1 mm, an outer diameter of 0.3 mm, and a length of 28 mm and made so as to store this coiling state, were fixed at first ends thereof to respective movable parts, so that they acted in opposition to one another via each movable part. The other ends were attached to stainless actuator fixing member rings 6, 6 (inner diameter of 1.0 mm, and outer diameter of 1.2 mm). Pull wires 14, 24, 34 and 44 were attached at first end thereof to the movable parts 13, 23, 33 and 43 to form actuator units U1, U2, U3 and U4. When they were applied to the bending endoscope of Example 1, actuator units U1, U2, U3 and U4 were set to cover the tubular body, and the length of the shape memory alloy coil springs was adjusted to 39 mm, thereby attaining bending of about 60 degrees in four directions.

EXAMPLE 7

Figure 7:
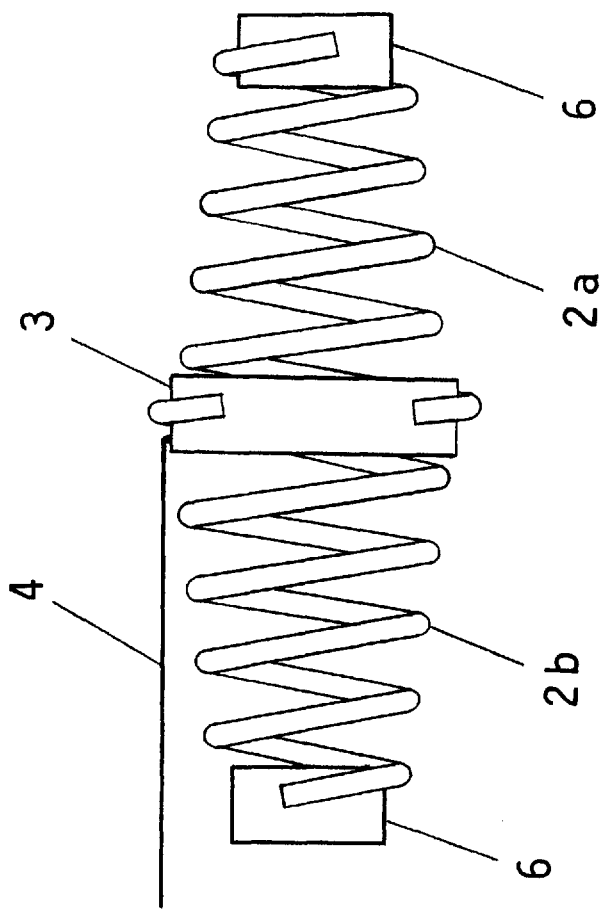
FIG. 7 is a perspective view showing still another actuator unit of the bending mechanism of the present invention.

This is an example wherein a tapered shape memory alloy coil was used for heating by light. The actuator unit is shown in FIG. 7. The movable part 3 was a stainless ring having an inner diameter of 0.9 mm and an outer diameter of 1.0 mm, and the actuator fixing members 6, 6 were stainless rings having an inner diameter of 0.5 mm and an outer diameter of 0.6 mm. The shape memory alloy coils 2*a* and 2*b* were each formed with a strand diameter of 0.3 mm, a length of 15 mm and were made so as to store this coiling state. The coils were set in a tapered state with a 0.6 mm coil inner-diameter at the actuator fixing member side and a 1.0 mm diameter at the movable part side, so that they act in opposition to each other via the movable part. The pull wire 4 was attached at one end thereof to the movable part 3. Though not shown, an optical fiber for heating the shape memory alloy coils was formed at the proximal end portion of shape memory alloy coil 2*a*. They were applied to the outer periphery of the image scope (outer diameter of 0.4 mm) shown in Example 1 and used as a bending endoscope. The length of each shape memory alloy coils 2*a* and 2*b* was adjusted to 20 mm, thereby attaining bending of about 50 degrees when the original shape of shape memory alloy coil 2*a* was recovered by laser irradiation from the optical fiber.

The bending endoscopes fabricated in Examples 1–7 were activated by heating the shape memory alloy coil springs. As a result, bending of about 40–60 degrees was achieved from the position before heating without buckling at the bending part during operation or non-operation. While the bending angle was 40–60 degrees, such can be varied by appropriately selecting the material and size of the actuators, as well as the material and size of the tubular body and image scope.

EXAMPLE 8

A stereoscope of FIG. 8 was fabricated. Two shape memory alloy coil actuators 2a and 2b were fixed at first ends thereof to support plates 16, 16 which also supported image scopes 5, 5, and at second ends thereof to movable part 3 formed between the support plates 16, 16 and movable in the lengthwise direction of the scope to allow opposing action of the actuators. The support plates had holes for passing image scopes therethrough at positions toward an outer periphery from the actuators 2a and 2b, so as to support the image scopes 5, 5 as mentioned above. Each of the support plates had a ring shape to secure a space inside the stereoscope. The image scopes 5, 5 passed through the holes formed in the support plates 16, 16 and projected from the distal end side support plate 16 toward the distal end. They were placed in a parallel relationship to interpose actuators 2a, 2b and movable part 3 therebetween. The support plates were fixed to the image scopes. In this way, a part of the image scope located at the distal end side from the support plate 16 became a bending part which could bend. The pull wires 4, 4 were fixed at first ends thereof to the movable part 3 and, at second ends thereof, to the distal end sides of image scopes 5, 5. The shape memory alloy coils were treated to store the close coiling state beforehand and were attached to the support plates and the movable part upon stretching.

The prepared stereoscope functioned according to the following principle. The shape memory coil 2a at the proximal side was heated to recover its original close coiling state. As a result, the movable part moved to the proximal side (downward in the Figure) and pulled wires 4 and 4. Consequently, the bending parts of image scopes 5, 5 bent to change their angles. A treatment such as superimposing of the images obtained from the two image scopes by an image processing device not shown here gives a stereoscopic image.

EXAMPLE 9

Figure 9:
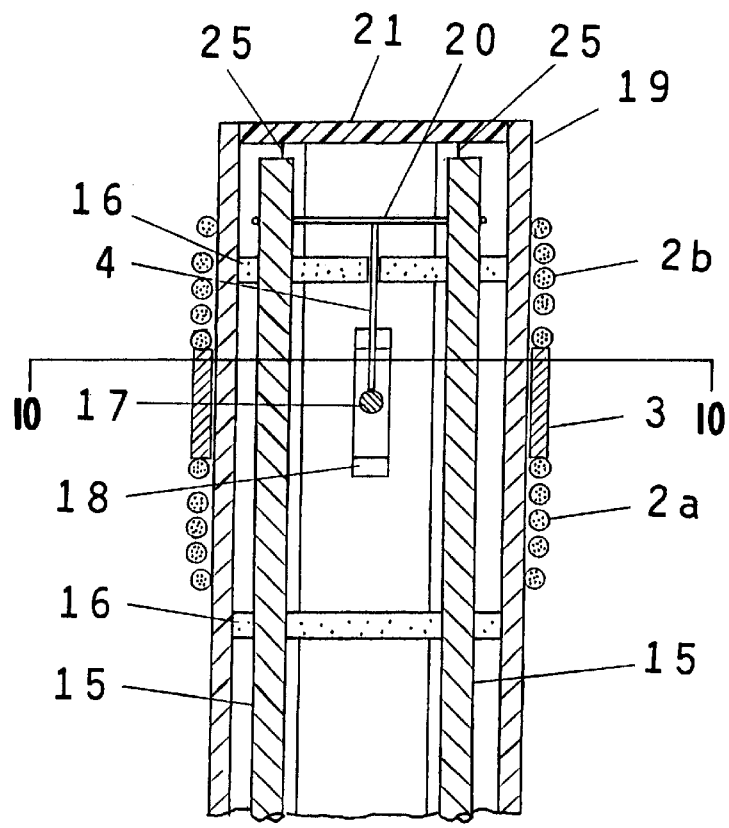
FIG. 9 is a lengthwise cross-sectional view of another embodiment of the stereoscope of the present invention.
Figure 10:
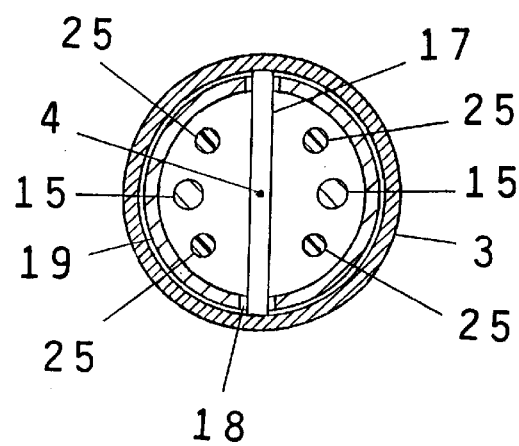
FIG. 10 is a cross-sectional view taken along line 10—10 of FIG. 9.

A stereoscope of FIGS. 9 and 10 was fabricated. FIG. 9 is a lengthwise cross-sectional view of the stereoscope of this Example. FIG. 10 is a cross-sectional view of FIG. 9 taken along line 10—10 of FIG. 9.

Specifically, two image guides 15, 15 were placed in a protection tube 19 at a certain spacing, and they were fixed by support plates 16, 16-and a co-activation wire ring 20 which was hung on the two image guides at a distal side from the support plates. Note that the support plates had respective holes for passing therethrough image guides 15, 15, four light guides 25 and pull wire 4. When a multifunctional scope was desired by forming various sensors, additional holes may be formed as appropriate. The protection tube 19 was provided with a stroke control window 18 in advance.

The two shape memory alloy coils 2a and 2b were fixed, at first ends, to movable ring 3 and were disposed on the outer periphery of the protection tube, 19. The two shape memory alloy coils 2a and 2b were stretched and fixed at the other end to the protection tube 19. A displacement limiting rod 17 was attached to movable ring 3 so as to extend orthogonally to a line connecting the two image guides 15, 15, and a pull wire 4 was attached, at one end, to the displacement limiting rod 17 and, at the other end, to the center of the co-activation wire 20. Four light guides 25 were formed in parallel with image guides 15, 15, and transparent cap 21 was set at the distal end thereof.

The prepared stereoscope functioned according to the following principle. The shape memory coil 2a was heated by a current from a power source (not shown) to recover its original close coiling state. As a result, movable part 3 moved downward in the figure, and pulled the wire 4. Consequently, a downward force was applied to the center portion of the co-activation wire 20, which in turn pulled the two image guides 15, 15, connected by the co-activation wire 20, toward the center of the scope to vary the angle of convergence. A procedure such as superimposing of the images obtained from two image guides gives a stereoscopic image.

EXAMPLE 10

Figure 11:
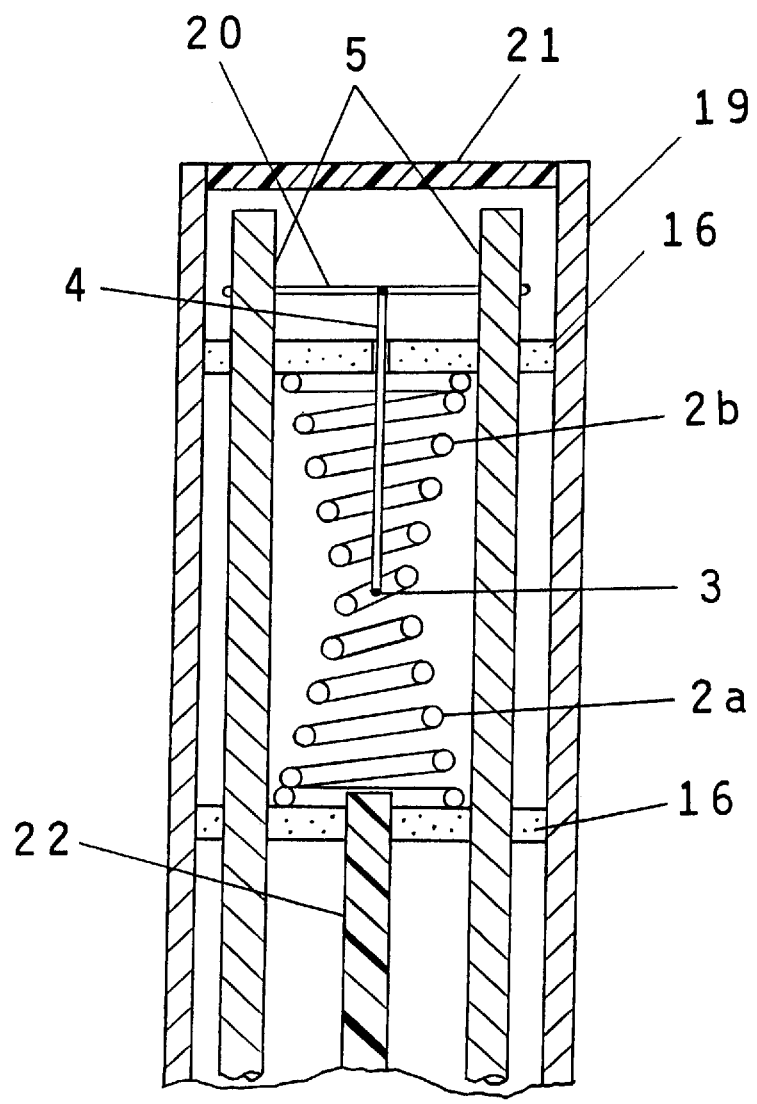
FIG. 11 is a lengthwise cross-sectional view of still another embodiment of the stereoscope of the present invention.
Figure 12:
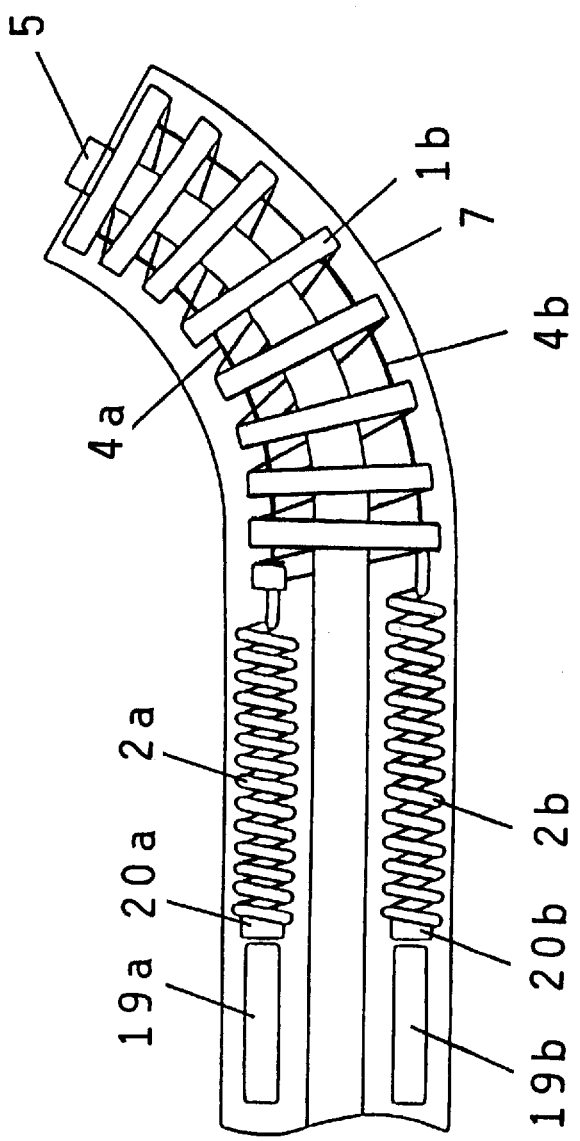
FIG. 12 is a lengthwise cross-sectional view of an articulation endoscope using a conventional articulation mechanism.

A stereoscope of FIG. 11 was fabricated. The shape memory alloy coil was disposed between support plates 16, 16 which also had fixed thereto an integrated shape memory alloy coil consisting of two actuators 2a and 2b and movable part 3, and support image scopes 5, 5. Thus, the ends of the shape memory alloy coil were fixed to the support plates 16, 16, respectively. Holes were formed through the support plates 16, 16, nearer to the outer peripheries thereof with respect to the coil attaching locations of the support plates 16, 16 for having the image scopes 5, 5 extend therethrough. The two image scopes 5, 5 passed through the holes and partially projected toward the distal end side of the scope beyond the support plate 16. The scopes were placed in parallel, with the shape memory alloy coil interposed therebetween. A co-activation wire ring 20 was set on the two image scopes at a distal side outside of the support plates. The pull wire 4 was fixed, at one end, to the center portion in the lengthwise direction of the shape memory alloy coil and, at the other end, to the center portion of the co-activation wire 20 between the image scopes. To make possible heating of the entire proximal actuator 2a by light, the shape memory alloy coil was tapered to have a minimum diameter at the center portion in the lengthwise direction, and a maximum diameter at both ends. An optical fiber 22 for laser irradiation was disposed at the proximal end side of the shape memory alloy coil.

This taper structure permitted irradiation of the light in the entirety of the actuator 2a, and materials with poor thermal conduction, such as TiNi alloy, could be heated in the entirety of the actuator. Inasmuch as the movable part and actuators were integrally formed, the connection between both members was not necessary, and connection of lead wires was also unnecessary due to the use of heating by light. As a result, fabrication was facilitated and a narrower scope could be obtained with fewer constituent elements.

As explained in the foregoing, the bending mechanism of the present invention is free of displacement of the movable part when bending action is not needed, since two actuators are used which antagonize (i.e. act in opposition to) each other via the movable part. Moreover, the bending part is not normally subjected to force, since the pull wire is not activated in this state, whereby buckling of the bending part can be eliminated. A simple structure the of activator unit, which is the most significant part of the bending mechanism, facilitates reduction of the size of the structure.

What is claimed is:

1. A bending mechanism comprising:

an elongated body having a first end portion and a second end portion and including an elongated bending part having a first end portion and a second end portion;

a movable part movably mounted for movement in a lengthwise direction of said elongated body;

two actuators, at least one of which is a shape memory element, operably connected to said movable part so as to act in opposition to one another via said movable part;

a pull wire having a first end and a second end and extending in a lengthwise direction along said bending part;

wherein said first end of said pull wire is fixed to said first end portion of said bending part; and wherein said second end of said pull wire is fixed to said movable part.

2. A bending mechanism as recited in claim 1, wherein both of said two actuators are shape memory elements.

3. A bending mechanism as recited in claim 2, wherein said two actuators constitute a first actuator and a second actuator;

said pull wire constitutes a first pull wire and is operably connected to said first actuator so that said first actuator is operable, upon actuation, to pull said first pull wire and cause bending of said bending part in a first direction; and a second pull wire is provided and is operably connected to said second actuator so that said second actuator is operable, upon actuation, to pull said second pull wire and cause bending of said bending part in a second direction different than said first direction.

4. A bending mechanism as recited in claim 1, wherein said pull wire is formed of a shape memory alloy;

at least one additional pull wire is provided and is formed of a shape memory alloy; and said pull wires can be heated separately.

5. A bending mechanism as recited in claim 1, wherein said shape memory element comprises a shape memory alloy coil.

6. A bending mechanism as recited in claim 1, wherein each of said actuators comprises plural shape memory elements.

7. A bending mechanism as recited in claim 1, wherein said two actuators, said movable part and said pull wire together constitute one of a plurality of similar actuator units; and for each of said actuator units, said pull wire is set at a predetermined circumferential position and extends along said lengthwise direction of said bending part.

8. A bending mechanism as recited in claim 7, wherein one of said actuator units is provided radially inwardly of another one of said actuator units.

9. A bending mechanism as recited in claim 7, wherein said movable parts of said actuator units, respectively, are circumferentially aligned so as to constitute a divided movable ring.

10. A bending mechanism as recited in claim 1, wherein said movable part is mounted in a location nearer to said second end portion of said bending part than said first end portion of said bending part.

11. A bending mechanism as recited in claim 1, wherein wherein said elongated body comprises a tubular body.

12. A bending mechanism as recited in claim 1, wherein said actuators are respectively disposed on opposite sides of said movable part.

13. A stereoscope comprising:

two elongated image guides spaced apart at a certain distance, each of said image guides having a first end portion and a second end portion and including an elongated bending part having a first end portion and a second end portion;

a movable part movably mounted for movement in a lengthwise direction of said image guides;

two actuators, at least one of which is a shape memory element, operably connected to said movable part so as to act in opposition to one another via said movable part;

at least one pull wire having a first end and a second end and extending in a lengthwise direction along said bending parts;

wherein said first end of said at least one pull wire is fixed to said first end portions of said bending parts; and wherein said second end of said at least one pull wire is fixed to said movable part;

whereby operation of said at least one pull wire activates said bending parts of said image guides, respectively.

14. A bending mechanism as recited in claim 13, wherein both of said two actuators are shape memory elements.

15. A bending mechanism as recited in claim 13, wherein said shape memory element comprises a shape memory alloy coil.

16. A bending mechanism as recited in claim 13, further comprising a coupling wire linking said first end portions of said bending parts;

wherein said first end of said at least one pull wire is connected to said coupling wire.

17. A bending mechanism as recited in claim 13, wherein said at least one pull wire comprises two pull wires;

said first ends of said pull wires are respectively connected to said first end portions of said bending parts; and wherein said second ends of said pull wires are connected to said movable part.

18. A bending mechanism as recited in claim 13, wherein said actuators are respectively disposed on opposite sides of said movable part.

* * * * *